(12) United States Patent
Chang

(10) Patent No.: US 9,476,029 B2
(45) Date of Patent: Oct. 25, 2016

(54) EX VIVO DEVELOPMENT, EXPANSION AND IN VIVO ANALYSIS OF A NOVEL LINEAGE OF DENDRITIC CELLS

(76) Inventor: Lung-Ji Chang, Gainesville, FL (US)

( * ) Notice: Subject to any disclaimer, the term of this patent is extended or adjusted under 35 U.S.C. 154(b) by 372 days.

(21) Appl. No.: 13/885,025

(22) PCT Filed: Nov. 14, 2011

(86) PCT No.: PCT/US2011/060560
§ 371 (c)(1),
(2), (4) Date: Aug. 29, 2013

(87) PCT Pub. No.: WO2012/065156
PCT Pub. Date: May 18, 2012

(65) Prior Publication Data
US 2013/0330310 A1 Dec. 12, 2013

Related U.S. Application Data

(60) Provisional application No. 61/413,436, filed on Nov. 13, 2010.

(51) Int. Cl.
| | |
|---|---|
| *C12N 5/071* | (2010.01) |
| *C12N 5/00* | (2006.01) |
| *C12N 5/02* | (2006.01) |
| *C12N 5/0784* | (2010.01) |
| *A61K 35/15* | (2015.01) |
| *A61K 39/00* | (2006.01) |

(52) U.S. Cl.
CPC ............ *C12N 5/0639* (2013.01); *A61K 35/15* (2013.01); *A61K 39/0011* (2013.01); *A61K 2039/5154* (2013.01); *A61K 2039/5156* (2013.01); *C12N 2501/052* (2013.01); *C12N 2501/125* (2013.01); *C12N 2501/145* (2013.01); *C12N 2501/22* (2013.01); *C12N 2501/2302* (2013.01); *C12N 2501/2304* (2013.01); *C12N 2501/2307* (2013.01); *C12N 2501/2315* (2013.01); *C12N 2501/25* (2013.01); *C12N 2501/26* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 2004/0072347 A1* | 4/2004 | Schuler | C12M 23/08 435/372 |
| 2006/0002899 A1* | 1/2006 | Rice | C12N 5/0639 424/93.7 |
| 2006/0134783 A1* | 6/2006 | Fong | A61K 35/12 435/372 |

OTHER PUBLICATIONS

Saikh et al., 2001, Clin. Exp Immunol. vol. 126: 447-455.*
Feugier et al., 2002, J. Hemo. Stem Cell vol. 11: 127-138.*
Feugier et al., 2005, Stem Cell Dev. vol. 14: 505-516.*
Bordeaux-Rego et al., 2010, Stem Cell Dev. vol. 19: 413-421.*

* cited by examiner

*Primary Examiner* — Amy Juedes
(74) *Attorney, Agent, or Firm* — Wolf, Greenfield & Sacks, P.C.

(57) ABSTRACT

Disclosed herein are new methods of producing a novel line of dendritic cells. The method comprises subjecting a sample of hematopoietic stem/precursor cells to a first feeder culture system that is supplemented with a first set of factors and a second feeder culture system supplemented with a second group of factors. The disclosure also pertains to new cell types that may be used as cancer immunotherapy.

7 Claims, 6 Drawing Sheets

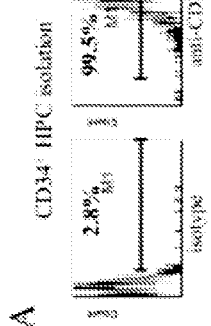
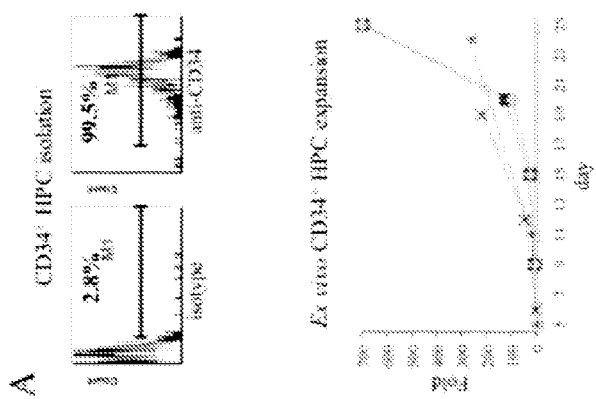
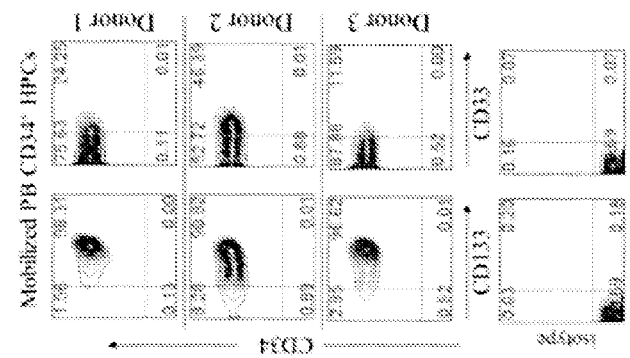
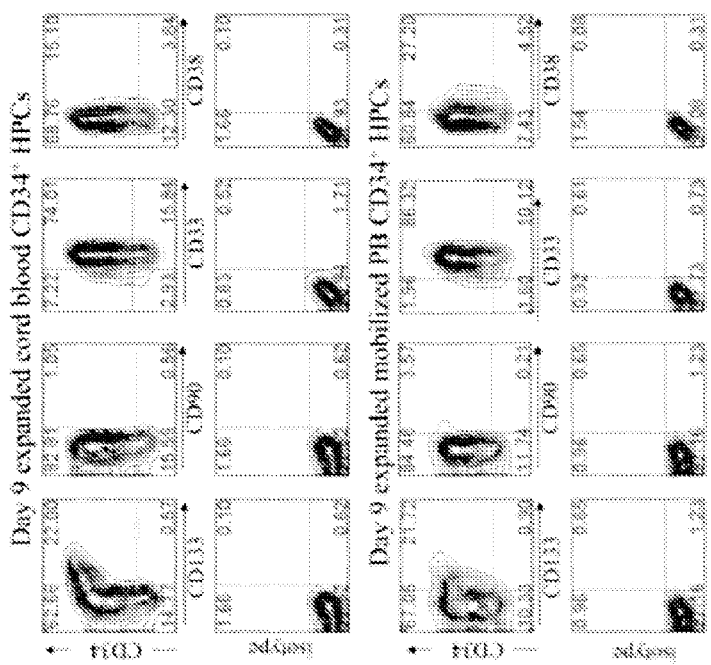
Fig 2

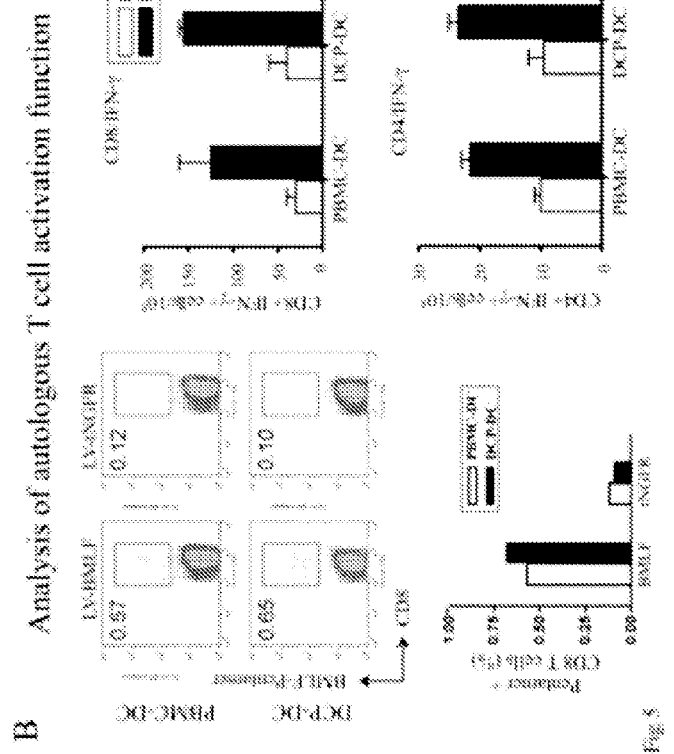
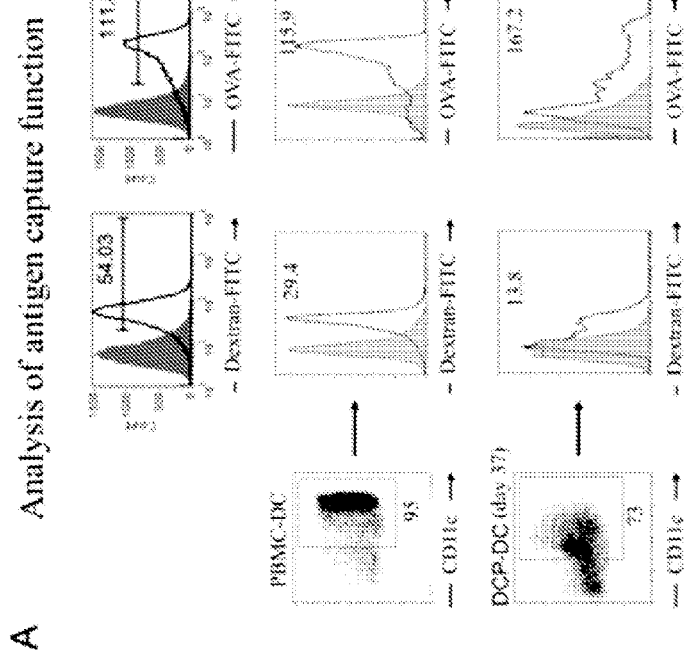
Fig. 5

EX VIVO DEVELOPMENT, EXPANSION AND IN VIVO ANALYSIS OF A NOVEL LINEAGE OF DENDRITIC CELLS

CROSS-REFERENCE TO RELATED APPLICATIONS

This application is related to U.S. Provisional Application No. 61/413,436; filed Nov. 13, 2010, to which priority is claimed under 35 USC 119, and which is incorporated herein in its entirety.

STATEMENT REGARDING FEDERALLY SPONSORED RESEARCH

The presently disclosed subject matter was made with U.S. Government support under grant number HL 59412 awarded by the National Institutes of Health. The U.S. government has certain rights in the invention.

BACKGROUND

Dendritic cells (DCs) initiate primary and memory immune responses as well as activate innate immunity and therefore, play a pivotal role in immunotherapy [1]. Accounting for only 0.02-0.2% of the total white blood cells, the number of DCs that can be isolated from peripheral blood is limited [2]. When cultured with supplement of GM-CSF and IL-4, PBMCs or CD14-selected monocytes generate DCs at about 50% of the starting cell number. Furthermore, patients with cancer or chronic infections often suffer from a compromised immune system with increased myeloid suppressor cells and dysfunctional DCs [3-9].

The developmental origin and tissue distribution of various lineages of human versus mouse DCs are still not well defined [10-15]. Transgenic mouse studies have reported several transcription factors implicated in regulating DC differentiation, which include zinc finger protein Ikaros, PU.1, relB, the helix-loop-helix (HLH) transcription factor inhibitor of DNA binding or differentiation 2 (Id2), interferon regulatory factor (IRF) 4 and 8, the Ets-domain transcription factor Spi-B, and the Notch family of proteins [14, 16]. In addition, growth factors such as Flt3L, KL, TPO, TNFα, GM-CSF, IL-3, IL-4, and IL-6 have been shown to promote development and maturation of DCs [17-20].

Growth factors such as KL and Flt3L appear to be strictly required for the generation of DC progenitors from HPCs in culture [21]. In the laboratory, GM-CSF and IL-4 are routinely used to generate DCs from adherent PBMCs, and GM-CSF and TNF-α can induce differentiation of HPCs into interstitial DCs and Langerhan's cells in 12-14 days [22]. GM-CSF and IL-15, on the other hand, drive DC differentiation from monocytes and bone marrow (BM) but the role of IL-15 in myeloid lineage development remains poorly understood [23, 24]. IL-15 is a member of the γC receptor family of cytokines which is expressed by a variety of cell types important to the survival of fibroblasts, T cells and natural killer cells. IL-15 has been shown to promote the survival of mature DCs through an autocrine antiapoptotic mechanism [25, 26], and IL-15-derived DCs are reported to display Langerhans cell-like features with strong T cell activation potential [23, 24, 27, 28].

BRIEF DESCRIPTION OF THE DRAWINGS

FIG. 2. Expansion of CD34+ HPCs and phenotype analysis. (A) Ex vivo expansion kinetics of CD34+ HPCs in LSC culture. HPCs were purified using anti-CD34 Ab magnetic beads and analyzed with anti-CD34, anti-CD133, and anti-CD33 Abs by flow cytometry. The expansion kinetics on LSC-KFT63b of HPCs from four donors are plotted. (B) Flow cytometry analysis of hematopoietic progenitor and differentiation markers after HPC expansion in LSC culture for 9 days. Both cord blood and adult PB CD34+ HPCs were analyzed.

(B) Kinetic analysis of myeloid cell differentiation markers. The expression kinetics of molecular markers for myeloid cells including PU.1, Langerin, Id2, hIL7R-α, CCL17, hCCR6, and E-cadherin (E-CAD) in the developing human DCPs were examined by RT-PCR. (C) Expression kinetics of DC surface markers of the DCPs based on flow cytometry analysis. (D) Surface phenotype of day 37 DCPs from the LSC-KFT-GM15 culture. The number inside each of the flow graph represents percentage of positive cells.

Figure 4:
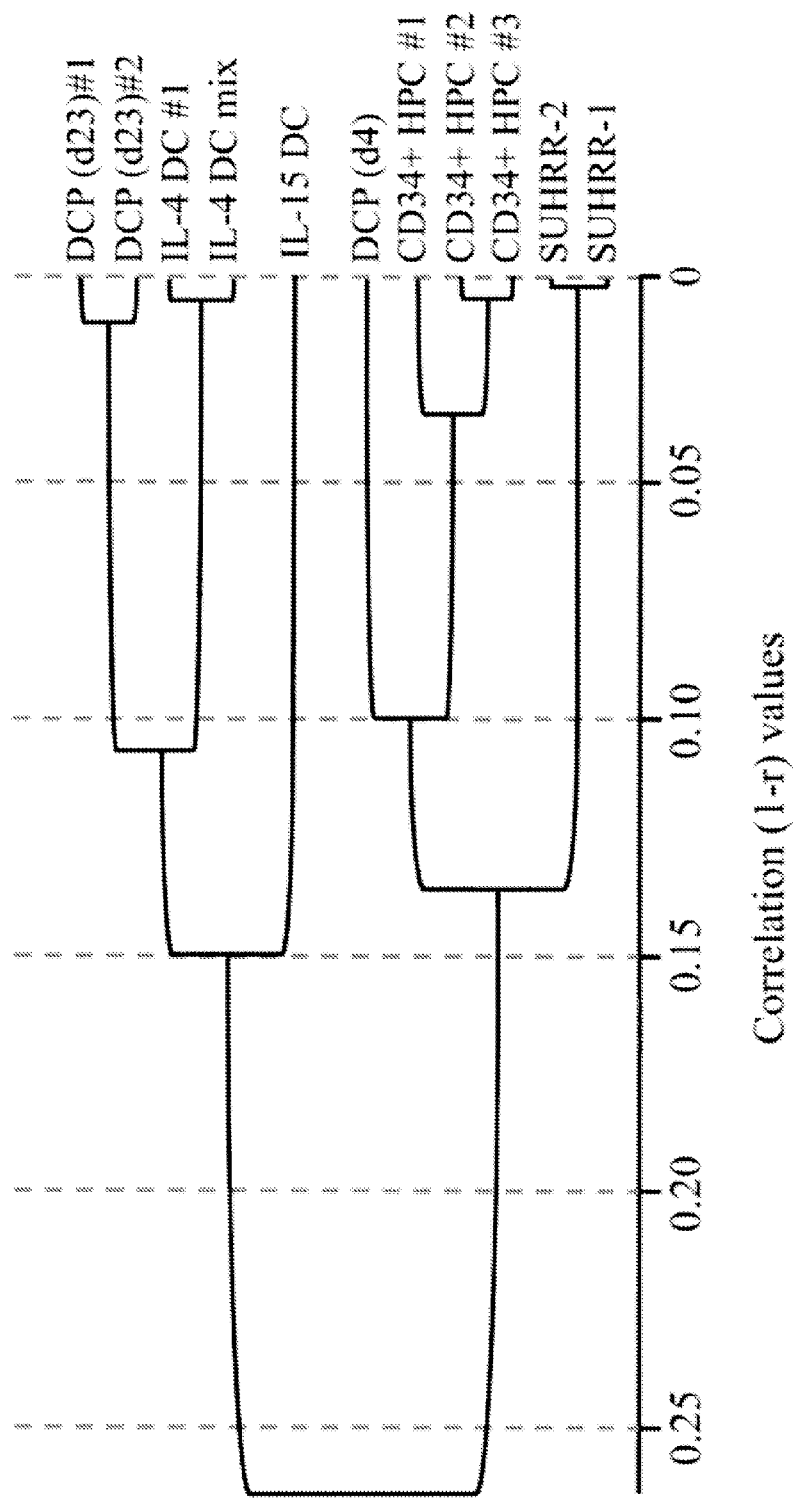

FIG. 4. Microarray dendogram analysis of the ex vivo differentiated DCPs. Gene expression profiles of CD34$^+$ HPC-derived DCPs at early (day 4) and late (day 23) time points after differentiation in LSC-KFT-GM15 were examined using Illumina human whole-genome RefSeq 8 expression BeadChip containing 24,000 genes. The related cell types are grouped in clusters in the dendogram, including day 4 and day 23 DCP specimens, IL-4 DC specimens (including a mixed IL-4 DCs from five donors), IL-15 DCs, and three CD34+ HPC specimens. Stratagene universal human reference RNA (SUHRR) was included for quality control.

FIG. 5. Functional analyses of the ex vivo expanded DCPs. (A) Analysis of antigen capture function of the ex vivo derived DCPs. Antigen capture was demonstrated using dextran-FITC or OVA-FITC particle internalization followed by flow cytometry analysis. Examples of FITC-positive control PBMC-derived DCs are shown at top; antigen capture was detected at 37° C. but not at 4° C. (B) Analysis of antigen-specific T cell stimulation function. DCs were transduced with LVs encoding a control truncated NGFR (tNGFR) protein or BMLF protein of EBV, and incubated with autologous T cells (from the same HLA-A*0201 donor) for 10-12 days. The BMLF-specific A*0201 TCR bearing T cells were detected using a PE-conjugated MHC-peptide pentamer by flow cytometry (left panel). Antigen-specific effector function was analyzed based on intracellular expression of IFN-γ as described in Materials and Methods.

Figure 6:
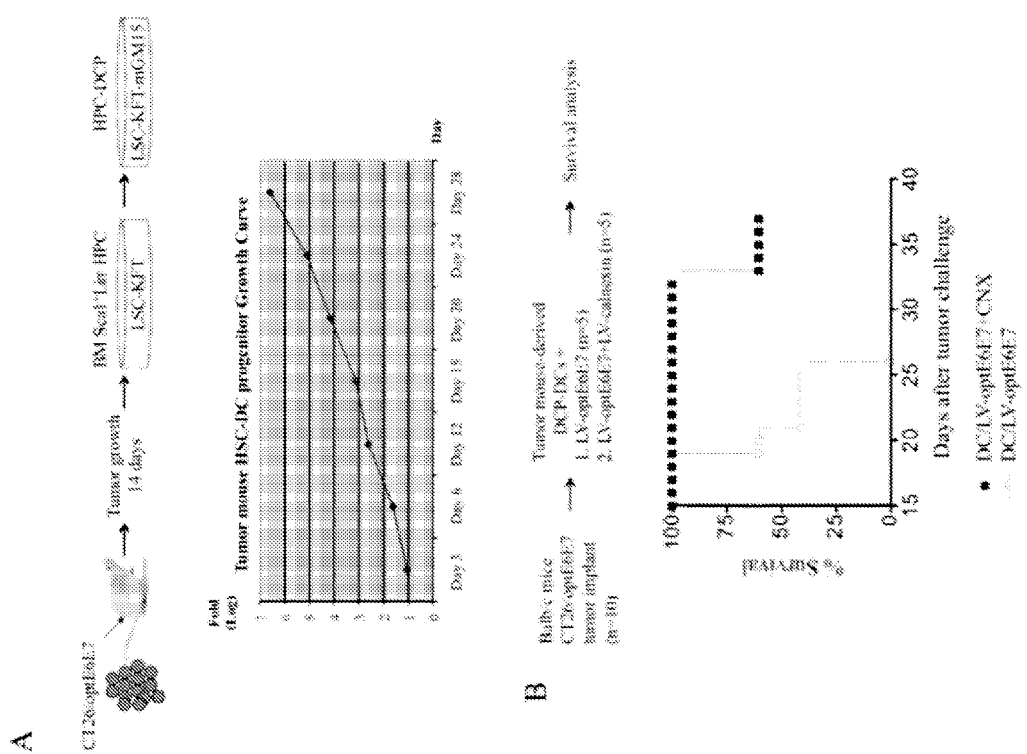

FIG. 6. DCPs derived from BM HPCs of tumor-bearing mice suppress tumor growth in vivo. (A) Ex vivo expansion of DCPs from BM HPCs of tumor-bearing Bulb/c mice. Balb/c mice were injected with CT26/optE6E7 tumor cells, and after 14 days, BM HPCs (Sca1$^+$/Lin$^-$) were harvested and cultured on LSC-KFT cells. After ten days, the expanded HPCs were transferred to LSC-KFT-mGM15 to generate DCPs. A representative mouse DCP expansion growth curve is shown. (B) Suppression of tumor growth in Balb/c mice immunized with LV-modified DCPs. CT27/optE6E7 tumor cells were first established in Balb/c mice. The mice were immunized with the ex vivo expanded DCPs, which were derived from the BM HPCs of CT26/optE67 tumor-bearing Balb/c mice. Two types of LV-modified DCs were tested: DCs transduced either by LV-optE6E7 alone or by LV-optE6E7 plus LV-calnexin. The percentages of survival of the two groups of mice are illustrated. Survival was based on tumor size smaller than 1 cm$^3$ without lesions.

DETAILED DESCRIPTION

Although DCs can be derived from PBMCs, BM or embryonic stem cells, the source and the amount of these progenitor cells are restricted. While ex vivo DC development and expansion approaches have been attempted, only a moderate number of DCs can be generated with the most efficient system reporting about 94 fold expansion of DCs from BM cells [29, 30]. The scarcity and the variability of the various DC subsets have significantly hindered fundamental studies of this important lineage of immune cells. Innovative strategies that can reproducibly generate a large amount of functional DCs from a limited number of progenitor/stem cells are urgently needed.

Disclosed herein is a novel ex vivo culture system that combines expansion of HPCs and differentiation of a unique lineage of DC progenitors (DCPs). This system supports expansion and development of both human and mouse HPCs and DCs. The total number of DCs generated under this system reached more than five orders of magnitude in 30-40 days, and the ex vivo differentiated DCs displayed antigen capture, T cell activation and tumor suppression functions similar to that of the peripheral blood and BM-derived DCs. Thus, a large number of autologous HPCs and DCs can now be routinely generated from a small number of CD34$^+$ HPCs for the study of immune cell development with potential of translational applications.

Embodiments of the invention relate to a new method of production a new line of cells having properties of dendritic cells (DCs) and DC progenitor cells (DCPs). Dendritic cells (DCs) play a key role in innate and adaptive immunity but the access to sufficient amount of DCs for basic and translational research has been limited. Provided herein is a novel ex vivo system to develop and expand DCs from hematopoietic stem/progenitor cells (HPCs). Both human and mouse HPCs were expanded first in feeder culture supplemented with c-Kit ligand (KL, stem cell factor, steel factor or CD117 ligand), Flt3 ligand (fms-like tyrosine kinase 3, Flt3L, FL), thrombopoietin (TPO), IL-3, IL-6, and basic fibroblast growth factor (bFGF), and then in a second feeder culture ectopically expressing all above growth factors plus GM-CSF and IL-15. The techniques described herein can be implemented for human, and non-human animal stem cells, such as HPCs.

When using the new dual culture system, CD34$^+$ HPCs differentiated toward DC progenitors (DCPs), which expanded more than five orders of magnitude. The DCPs showed myeloid DC surface phenotype with up-regulation of transcription factors PU.1 and Id2, and DC-related factors homeostatic chemokine ligand 17 (CCL17) and beta-chemokine receptor 6 (CCR6). Multiplex ELISA array and cDNA microarray analyses revealed that the DCPs shared some features of IL-4 and IL-15 DCs but displayed a pronounced proinflammatory phenotype. DCP-derived DCs showed antigen-uptake and immune activation functions analogous to that of the peripheral blood-derived DCs. Furthermore, bone marrow HPC-derived DCP vaccines of tumor-bearing mice suppressed tumor growth in vivo.

This novel approach of generating DCP-DCs, which are different from known IL-4 and IL-15 DCs, overcomes both quantitative and qualitative limitations in obtaining functional autologous DCs from a small number of HPCs with great translational potential.

According to one embodiment, disclosed herein is method of producing a lineage of DC cells that includes culturing a population of hematopoietic stem/progenitor cells (HPCs) in a feeder culture supplemented with kit ligand (KL); fms-like tyrosine kinase 3 ligand (FL); thrombopoietin (TPO); IL-3; IL-6 and/or basic fibroblast growth factor (bFGF). The HPCs are cultured under conditions to produce a population of first expanded cells and then the first expanded cells are cultured in a second feeder culture ectopically expressing KL, FL, TPO, GM-CSF, and IL-15 under conditions to produce DC progenitor cells. According to a more specific embodiment, the DC progenitor cells are cultured in media in supplemented with GM-CSF and IL-15 under conditions to produce a population of cells having a phenotype similar to myeloid DCs.

Another embodiment disclosed herein pertains to a sample of DCPs produced by methods taught herein.

According to another embodiment, disclosed herein is method of treating a patient in need. The method involves administering a therapeutically effective amount of a sample of DCP cells produced according methods taught herein, wherein the patient in need is one who has cancer or infection related condition. In a specific embodiment, the patient in need is one who has multiple myeloma, acute myeloid leukemia, acute lymphoblastic leukemia, Hodgkin's lymphoma and glioblastoma. According to another method, the DCPs are derived from HPS that are autologous to or compatible with a patient in need.

EXAMPLES

Example 1

Methods

Cells and Mice

CD34$^+$ cells used in this study were purified from BM, mobilized peripheral blood (MPB) or cord blood (CB) using magnetic beads (Miltenyi Biotec) following the manufacturer's instructions or purchased from AllCell Inc. (San Mateo, Calif.), Cambrex (Baltimore, Md.) and National Disease Research Interchange (Philadelphia, Pa.). Buffy coats of peripheral blood of healthy donors were purchased from Civitan Blood Center (Gainesville, Fla.). PBMCs were isolated from buffy coats of healthy donors or from blood of cancer patients with approval of the Institutional Review Board of University of Florida. B lymphoblastoid cell lines (BLCLs) were generated by transforming peripheral blood B lymphocytes with EBV as described previously [31]. The BLCLs were propagated in complete RPMI-1640 medium (Gibco, Grand Island, N.Y.) supplemented with 2 mM L-glutamine, 100 ug/ml streptomycin, 100 IU/ml penicillin and 10% heat inactivated fetal bovine serum (FBS) at 37° C. with 5% $CO_2$. The mouse fetal stromal cells were cultured in Minimal Essential Medium Alpha (Gibco, Grand Island, N.Y.) supplemented with 2 mM L-glutamine, 100 ug/ml streptomycin, 100 IU/ml penicillin and 20% heat inactivated FBS (Gibco) at 37° C. with 5% $CO_2$. CT26 mouse colon carcinoma cell line was purchased from ATCC (catalogue no. CRL-2638) and cultured in Dulbecco Modified Eagle's Medium (Gibco, Grand Island, N.Y.) supplemented with 2 mM L-glutamine, 100 ug/ml streptomycin, 100 IU/ml penicillin and 10% heat inactivated FBS (Gibco) at 37° C. with 5% $CO_2$. BALB/c mice were obtained from Jackson Laboratory (Bar Harbor, Me.) with approval from the Institutional Animal Care and Use Committee of University of Florida.

Antibodies and Reagents

Fluorescein isothiocyanate (FITC)-conjugated Abs to CD4, CD8, CD11c, CD33, CD34, CD38, CD86, IFN-γ, and HLA-DR, phycoerythrin (PE)-conjugated Abs to CD4, CD8, CD11c, CD34, CD83, CD90, CD123, HLA-DR, IFN-γ, and TNFα, PerCP Cy5.5-conjugated Ab to CD8, CD33, PE-Cy7-conjugated antibodies to CD8, CD11b, CD11c, CD34, CD62L, CD40 and CD80, and allophycocyanin (APC)-conjugated Abs to CD1a, CD3, CD11c, CD14, CD33, CD69, CD83, CD90, CD133, IFN-γ and TNF-α were purchased from BD Pharmingen (San Diego, Calif.), eBioscience (San Diego, Calif.), Miltenyi Biotec (Auburn, Calif.), and Caltag Laboratories (Invitrogen, Carlsbad, Calif.) as listed in Supplemental Table 1. Isotype-matched antibodies were included as controls. HLA-A2 restricted, EBV BMLF1 GLC-peptide (amino acid 280-288, GLCTL-VAML) pentamer was purchased from Proimmune (Springfield, Va.).

Lentivector Preparation and Gene Transfer

Lentivectors (LVs) were constructed as described previously [32-34]. The growth factor cDNAs were amplified by PCR using primers designed to contain an optimized translation initiation sequence (-CCACC-5' to the initiation codon). The primers used in this study are listed in Supplemental Table 2. The amplified cDNAs were cloned into the self-inactivating pTYF plasmid behind the EF1α promoter. To generate feeder cells, mouse fetal stromal cells were multiply transduced with LVs at 10-50 infectious unit/cell in 12-well plates in a minimal volume of 0.3 ml per well. After 2 h, 0.5 ml of fresh media was added and cells were incubated at 37° C. overnight. The infected cells were continuously propagated for more than 50 passages and stable lentiviral transgene expression was confirmed. The mouse CT26 tumor cells and DCs were transduced with LVs encoding a codon-optimized human HPV E6-E7 fusion protein and the chaperone protein calnexin as previously described [35].

RNA Extraction, RT-PCR and Microarray Analysis

RNA was extracted using Tri-reagent (MRC Inc., Cincinnati, Ohio) and oligo$(dT)_{15}$-primed cDNA was made with MMLV reverse transcriptase (Promega Inc., Madison, Wis.). For semi-quantitative PCR, all reactions used the same serially diluted cDNA normalized to the mouse GAPDH (mGAPDH). The PCR amplification conditions were as follows: denaturing temperature, 95° C.; annealing temperature, 55-62° C.; extension temperature, 72° C.; the amplification cycles were 25-35 cycles. Products were resolved by agarose gel electrophoresis and visualized by ethidium bromide staining. The PCR primers used in this study are listed in Supplemental Table 2.

For gene expression microarray analysis, RNA samples were harvested from purified $CD34^+$ HPCs, ex vivo cultured DCPs, and adherent PBMC-derived IL-4 and IL-15 DCs. These RNA samples were analyzed using Illumina Human RefSeq-8 Expression BeadChips. RNA quantity was determined with the Agilent RNA 6000 Nano Kit and Bioanalyzer. All samples displayed 28S and 5.8S peaks indicating intact full length RNA. Synthesis of double-stranded cDNA and in vitro transcription were performed with the Ambion Illumina TotalPrep kit according to manufacturers' instructions. For each sample, input quantity for the first strand synthesis was normalized to 200 ng. After in vitro transcription reaction, yield of purified cRNA was assessed with the RiboGreen assay and quality was assessed with the Agilent Bioanalyzer. BeadChip hybridization, staining and scanning were performed according to Illumina whole genome expression for BeadStation. For each sample, input of cRNA was normalized to 1500 ng. As control, Stratagene Universal Human Reference (SUHR) RNA was labeled with the Ambion TotalPrep kit. The labeled cRNA was used as interchip hybridization replicates and showed strong correlation. Biological replicate pairs were analyzed and for unnormalized data, the linear $r^2$ was greater than 0.94 for all replicates.

Generation of Mature DCs and Antigen-Specific Immune Cells

PBMCs were isolated after Ficoll-Hypaque density centrifugation (Sigma Aldrich, St Louis, Mo.). After plastic adherence, the adherent cells were cultured in 50 ng/ml GM-CSF and 25 ng/ml IL-4 (eBiosource International, Inc. Camarillo, Calif.) in serum-free AIM-V medium (Invitrogen, San Diego, Calif.) to generate immature DCs Immature DCs were transduced with LVs, and treated with LPS (1 ug/ml) and TNFα (20 u/ml) for 24 hr to induce maturation. The mature DCs were loaded with 5 ug/ml of specific peptides. The non-adherent PBMCs were cocultured with irradiated (10 Gy) mature DCs, at a 20:1 ratio, in AIM-V supplemented with IL-2 (12.5 U/ml) and IL-7 (10 ng/ml) in 24-well plates. At day 12 of coculture, the T cells were restimulated or harvested for analysis as previously described [36, 37]. The DCs of BALB/c mice were generated from BM of tumor-bearing mice and transduced with LVs as previously described [38].

Quantitative Cytokine and Chemokine Multiplexed Enzyme-Linked Immunosorbent Assay (ELISA) Arrays DCs were washed twice with PBS and cultured in AIM-V without growth factors and other supplements at a density of $10^6$ cells/ml for 24 hr. The supernatants were collected and delivered to Quansys Biosciences (Logan, Utah) for custom multiplexed sample testing as previously described [35]. Each sample was tested in triplicate. The list of cytokines and chemokines tested included: IL-1a, IL-1b, IL-2, IL-4, IL-5, IL-6, IL-8, IL-10, IL-12p70, IL-13, IL-17, IL-23, IFN-γ, TNF-α, TNF-β, Eotaxin, growth-related oncogene-alpha (GRO-α), monocyte chemotactic protein 1 (MCP-1), MCP-2, regulated upon activation, normal T-cell expressed and secreted cytokine (RANTES), 1-309 and thymus and activation-regulated chemokine (TARC).

Antibody and Pentamer Staining and Flow Cytometry

For antibody (Ab) staining, single-cells were suspended in PBS containing 2% FBS and 0.05% sodium azide and pre-incubated with anti-CD16/CD32 Ab for 10 min to block FcRs. Expression of cell surface markers was analyzed by standard four-color staining using FITC-, PE-, PE-Cy7 or PerCP and APC-conjugated primary Abs. To evaluate the expression of intracellular molecules, cells were washed and restimulated for 5 hr in the presence of brefeldin A (1 ug/ml) during the last 2.5 hr of culture. The stimulated cells were stained with anti-surface marker Abs, washed and permeabilized with the CytoFix-Cytoperm kit (BD Pharmingen), according to the manufacturer's instruction, then stained with anti-intracellular marker Abs, and analyzed by flow cytometry. For multimer staining, the resting T cells were stained with PE-labelled pentamer (Proimmune) for 12 min at room temperature, followed by FITC-labeled or PE Cy7-labelled anti-CD8 antibody for 30 min on ice and analyzed by flow cytometry. Data acquisition and analysis were done on a FACSCalibur and FACSAria using CellQuest and FACSDiva software, respectively (BD Biosciences, San Jose, Calif.), or Flowjo software (Tree Star, Inc. Ashland, Oreg.).

Analysis of Antigen Uptake

Immature DCs were harvested and washed with AIM-V twice and re-suspended in AIM-V at a concentration of $5 \times 10^5$ cells per ml. DCs were incubated with Dextran-FITC or OVA-FITC (Molecular Probes, Inc., Eugene, Oreg.) at 37° C. for 1 h; a parallel control was incubated at 4° C. for 1 h. Cells were washed three times with cold FACS buffer, resuspended in 100 ul of cold FACS buffer, stained with APC-conjugated anti-CD11c Ab (BD Biosciences, CA) and analyzed by flow cytometry.

In Vivo DC Vaccine Tumor Model

BALB/c CT26 colon cancer cells were transduced with LV-optE6E7 encoding a fusion protein of HPV 16 E6/E7 to generate the CT26-E6E7 cell line. The BALB/c mice were inoculated with $1 \times 10^5$ CT26-E6E7 tumor cells subcutaneously. Seven days later the mice were vaccinated with $2-5 \times 10^5$ immature DC/LV-optE6E7 or DC/LV-optE6E7/LV-calnexin derived from tumor-bearing mice, weekly for 2 weeks (n=5 per group). Tumor size was measured over time using calipers and mean tumor volume (in $mm^3$) was determined.

Statistical Analysis.

The statistical analysis was performed using Student's t-test and GRAPHPAD PRISM 4 software.

Example 2

Results

Expansion of CD34$^+$ HPCs and Development of DC Progenitors (DCPs)

Figure 1:
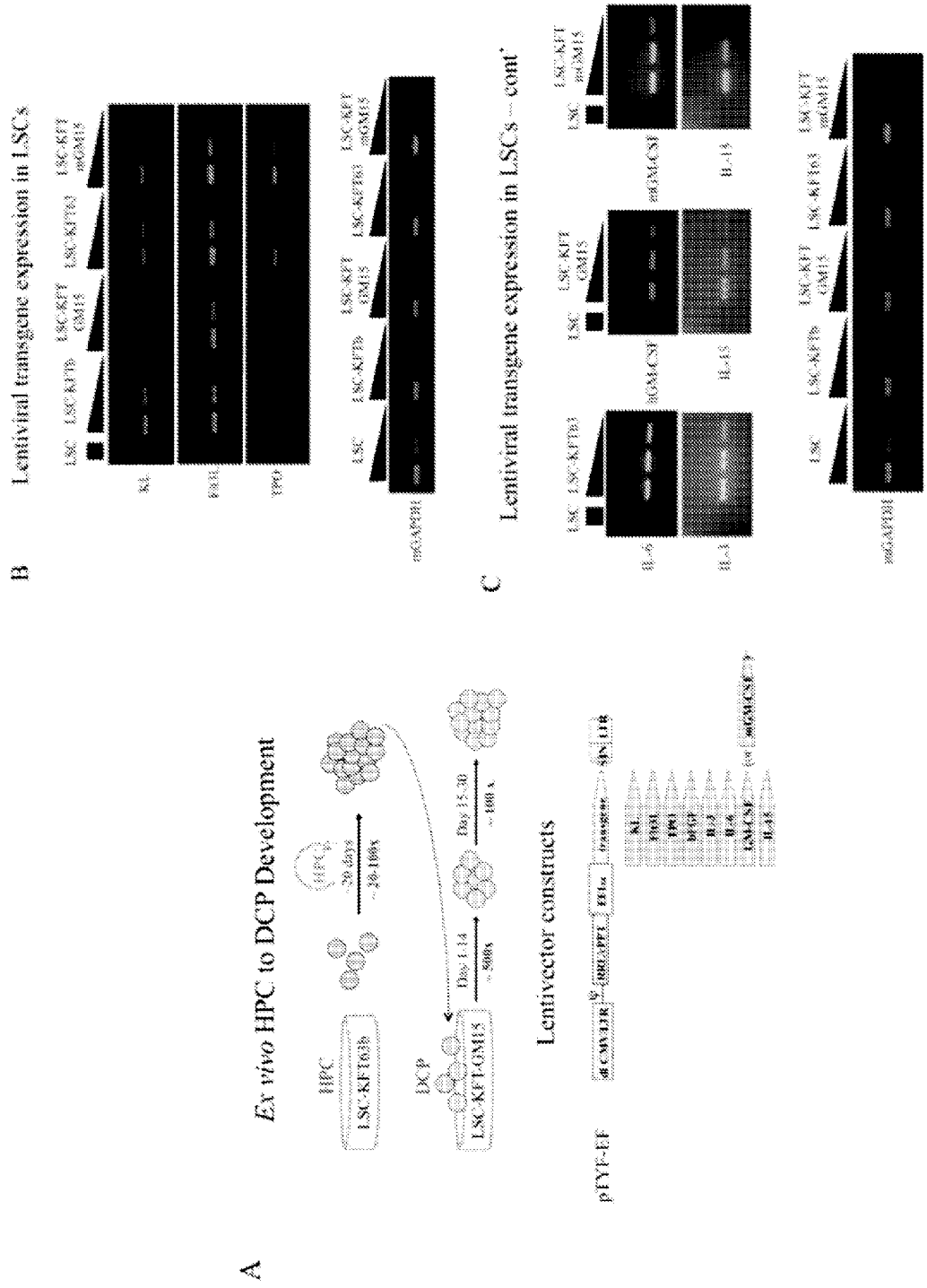
FIG. 1. The ex vivo HPC to DC expansion and development system. (A) Schematic representation of the LSC culture system and the lentivector constructs. The two LSC lines, LSC-KFT63b and LSC-KFT-GM15, produce the specified hematopoietic growth factors, which support the expansion of HPCs and DCPs. (B) and (C) Semi-quantitative RT-PCR analyses of lentiviral transgene expression in the LSC lines. All of the growth factor genes are human origin except for the mouse GM-CSF (mGM-CSF); the control endogenous mouse GAPDH (mGAPDH) gene expression is shown at bottom.

HPCs can expand in culture but have limited potential of maintaining hematopoietic stem cell phenotype and function [39]. A series of lentivector-modified stromal cell (LSC) lines were established to provide cell-free and cell-associated signals that can support continuous expansion of HPCs and differentiation of DCs (FIG. 1). The LSC lines include LSC-KFT (KL, Flt3L, TPO), LSC-KFTb (KL, Flt3L, TPO and bFGF), LSC-KFT63 (KL, Flt3L, TPO, IL-6, and IL-3) and LSC-KFT63b (KT, Flt3L, TPO, bFGF, IL-6, IL-3 and bFGF) for the expansion of HPCs, and LSC-KFT-GM15 (KL, Flt3L, TPO, GM-CSF and IL-15) and LSC-KFT-mGM15 (KL, Flt3L, TPO, mouse GM-CSF, and IL-15) for the differentiation and expansion of human and mouse DCs, respectively. LSC-KFT, LSC-KFTb, LSC-KFT63 and LSC-KFT63b supported HPC expansion to similar extents, and the total expansion fold varied with individual donors. Under this culture condition, HPCs consistently expanded twenty to one hundred-fold in twenty days, followed by more than one thousand-fold differentiation and expansion into DCPs in thirty days (FIG. 1A). This dual culture system supports expansion and development of DCs from both human and mouse HPCs.

To verify the expression of the various growth factors in LSCs, RNAs harvested from LSCs were analyzed by semi-quantitative RT-PCR (FIGS. 1B and 1C). It was confirmed that lentivector expression was stable even after 50 passages in these cell lines (data not shown). Highly enriched human CD34$^+$ HPCs derived from adult mobilized peripheral blood and BM expressed high level of hematopoietic progenitor marker CD133 and low level of CD33 (FIG. 2A). This culture system supported HPC expansion for both healthy donors and cancer patients; for example, adult peripheral blood (PB) HPCs expanded in LSC-KFT63b to about one hundred-fold in two to three weeks (FIG. 2A). Surface phenotype analysis indicated that the ex vivo expanded HPCs gradually lost progenitor markers (CD34, CD90, and CD133), which was accompanied by increased expression of myeloid differentiation markers CD38 and CD33 (FIG. 2B). Similar results have been obtained with mouse BM Sca1$^+$Lin$^-$ (lineage-minus) HPCs (data not shown).

Differentiation and Expansion of DCPs Toward Myeloid DC-Like Phenotype

To see if the LSC culture system can generate functional DCs, CD34$^+$ HPCs were first expanded in LSC-KFT63b. After an initial 20-40-fold expansion, the cells were transferred to LSC-KFT-GM15. The DCPs continued to expand several orders of magnitude in 30 days; they were then transferred to feeder-free culture supplemented with GM-CSF and IL-15 to generate functional immature DCs as illustrated in FIG. 3A.

Figure 3:
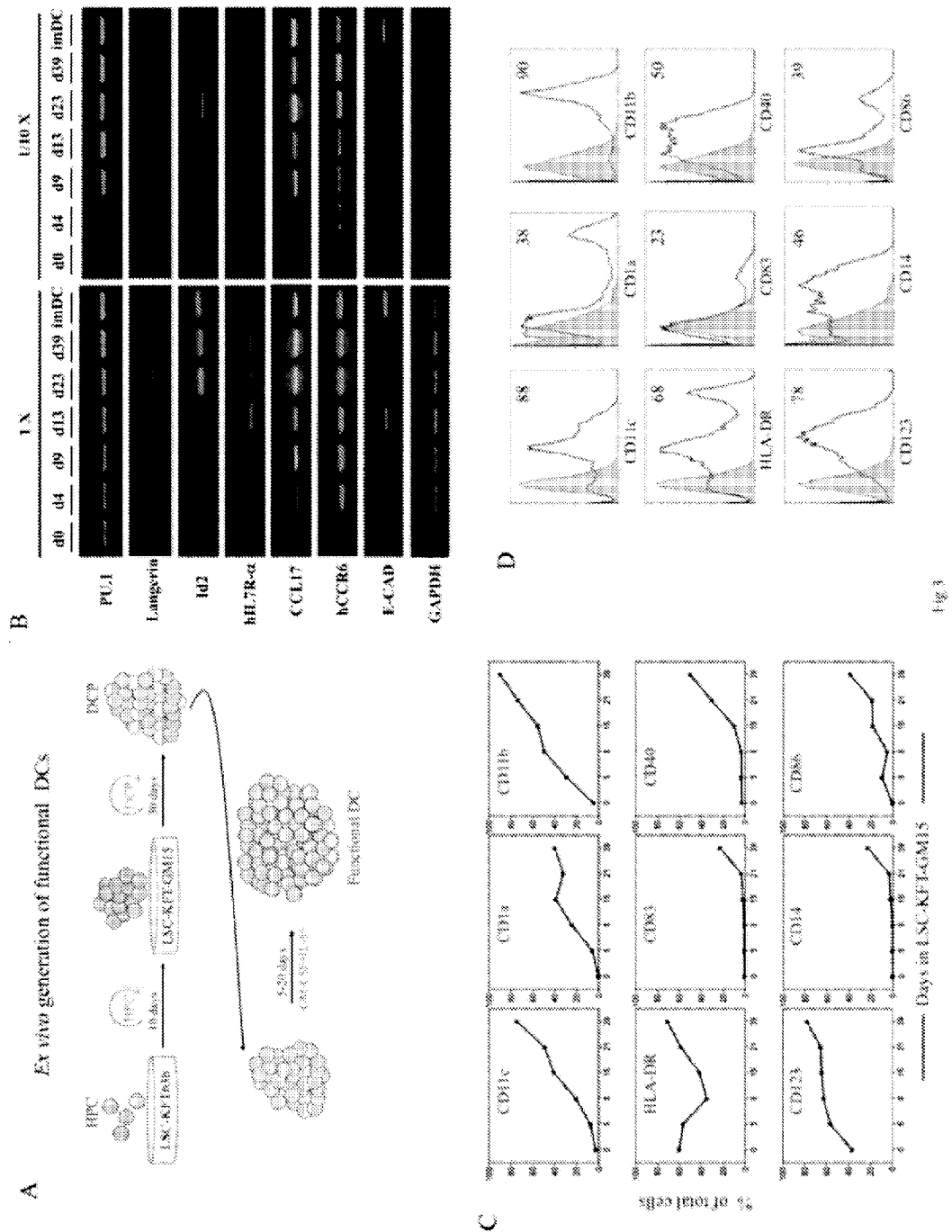
FIG. 3. Ex vivo generation of functional DCs. (A) Schematic illustration of expansion of human and mouse DCPs in culture. The human (CD34$^+$) or mouse (Sca1$^+$/Lin$^-$) HPCs were cultured on LSC-KFT63b for 10 days, and then transferred to LSC-KFT-GM15 (LSC-KFT-mGM15 for mouse cells) to expand for 30 days. The resulting DCPs were further cultured in medium supplemented with GM-CSF, IL-15 and growth factors to induce immature and mature DCs.

Analysis of myeloid and DC lineage differentiation markers including PU.1, Langerin, Id2, hIL7R-α, CCL17, hCCR6, and E-cadherin (E-CAD) of the DCPs from day 0, 4, 9, 13, 23 and 39 by semi-quantitative RT-PCR revealed a gradual increase in myeloid (PU.1) and DC differentiation markers (Id2, hIL7R-α, CCL17, and hCCR6), and a stochastic expression of differentiating Langerhans cell markers (Langerin or CD207 and E-CAD) as compared with monocyte-derived immature DCs (imDC, FIG. 3B). After 35 days, the DCPs displayed a differentiation profile similar to that of monocyte-derived imDCs, except for E-CAD, which was down-regulated. Kinetic analysis of monocyte and DC markers including CD14, CD11c, CD1a, CD11b, HLA-DR, CD83, CD40, CD123, and CD86 by flow cytometry showed that the ex vivo-expanded DCPs gradually differentiated toward mature DCs with increased expression kinetics of costimulatory molecules CD40, CD86, and DC maturation marker CD83 (FIG. 3C). A representative flow cytometry analysis of DC markers of day 39 DCPs is shown in FIG. 3D; at this time point, DCPs displayed increased activation and maturation markers resembling conventional mature DCs Similar results were observed with mouse DCPs expanded in the LSC-KFT-mGM15 culture (not shown).

We next examined the gene expression profile of the DCPs at different time points after differentiation from HPCs using Illumina BeadChip Human RefSeq-8 arrays. RNA samples were harvested from an early time point (day 4) and a late time point (day 23), and compared to RNAs harvested from CD34$^+$ HPCs and adherent PBMC-derived IL-4 and IL-15 DCs for comparison. Cluster analysis of unnormalized sample data showed that all biological replicates (two DCPs, two IL-4 DCs and three CD34$^+$ HPCs) sorted into the same groups (FIG. 4). Sample dendogram revealed that the day 4 differentiated DCPs displayed gene expression profile resembled CD34$^+$11PCs, whereas the day 23 differentiated DCPs displayed expression profile resembled IL-4 DCs (FIG. 4).

Cytokine and Chemokine Secretion Profiles of the Ex Vivo Generated DCs

As the morphology and surface marker expression pattern of the HPC-DCPs resembled myeloid DCs, we further examined the expression profile of inflammatory cytokines and chemokines. For comparison, we included the conventional IL-4 DCs and IL-15 DCs generated from adherent PBMCs. HPC-DCPs from adult BM CD34+ HPCs were kept in feeder-free culture supplemented with GM-CSF and IL-15 to generate immature DCs and then were treated with TNF-α and LPS to induce maturation, and after extensive washes, the cells were incubated in serum-free AIM-V medium at a density of $1 \times 10^6$ cells per ml for 24 hr. The supernatants were collected and analyzed using a multiplex ELISA array, which simultaneously measures a panel of 23 cytokines and chemokines [35]. The results from two donors are summarized in Table 1. We noted that HPC-DCPs displayed a trend of upregulation of inflammatory cytokines and chemokines, with marked increase in IL-1b, IL-6, GRO-α(CXCL1), 1-309 (CCL1), MCP-1 (CCL2), and MCP-2 (CCL8) compared with the traditional IL-4 DCs, suggesting that the DCPs have potent proinflammatory leukocyte chemotactic and activating functions. The overall cytokine and chemokine profile of DCP-derived DCs mimicked those of the IL-15 DCs except that the DCP-derived DCs produced reduced levels of IFN-γ and TNFα, at levels similar to those of the IL-4 DCs, with substantially increased expression of GRO-α and MCP-1.

Antigen Capture and T Cell Activation Functions of the Ex Vivo Generated DCs

Professional antigen presenting cells can uptake and process antigens and stimulate T cells. To examine these functions, we compared the ex vivo generated DCs with immature adherent PBMC-derived DCs (PBMC-DCs) for their antigen uptake function by feeding them with fluorescent DQ-OVA (OVA-FITC) and dextran-FITC particles. The PBMC-DCs captured fluorescent particles at 37° C. but not at 4° C., as demonstrated with flow cytometry. The day 37 DCP-DCs, which contained a large number of CD11c-positive cells, captured antigens as efficiently as did the PBMC-DCs (FIG. 5A).

To see if the DCP-derived DCs were capable of activating antigen-specific T cells, we set up a DC/T cell coculture system as previously described [31, 35, 37]. The DCs were transduced with LVs encoding a viral antigen, EBV BMLF (LV-BMLF), or a truncated self-antigen tNGFR (LV-tNGFR). After maturation, the DCs were cocultured with autologous monocyte-depleted PBMCs for 12 days to generate antigen-specific T cells. The activated T cells were restimulated with the corresponding DCs and incubated with a BMLF peptide-specific (GLCTLVAML, HLA-A2*-restricted) MHC pentamer to detect antigen-specific response. Both the DCP-DCs and the PBMC-DCs induced antigen-specific T cell response when transduced with LV-BMLF, but not LV-tNGFR (FIG. 5B, left panel). Intracellular staining for IFN-γ expression in CD4 and CD8 T cells confirmed that the DCP-DCs activated BMLF-specific T cells as effectively as did the PBMC-DCs (FIG. 5B, right panel). In contrast, the self-antigen tNGFR did not register a substantial response.

In Vivo Tumor Suppression Mediated by DCP-DCs Derived from Tumor-Bearing Mice

The above assays demonstrated that the HPC-derived DCs displayed antigen presentation and T cell activation functions similar to that of monocyte-derived DCs. To examine their therapeutic potential, experiment an experiment was designed using a previously established syngeneic mouse tumor model. BALB/c mice implanted with CT26 colon cancer cells expressing a codon-optimized Human Papilloma Virus 16 (HPV 16) E6 and E7 fusion protein (optE6E7) are protected through immunization with DCs transduced with LVs encoding optE6E7 and calnexin, a chaperone protein [31, 35]. To mimic situation in a cancer patient, DCPs were derived from BM of tumor-bearing mice to see if a protective anti-cancer immune response can be induced. FIG. 6A illustrates the strategy of generating DCPs from BM of tumor-bearing mice. CT26/optE6E7 tumors were first established in BALB/c mice, after confirming tumor growth, Sca1+Lin− HPCs were purified from BM of the tumor-bearing mice. The HPCs were expanded in the LSC culture system as described; a representative mouse DCP expansion curve is illustrated (FIG. 6A). The mouse DCPs expanded more than 6 orders of magnitude within 30 days. To generate DC vaccines, the tumor mouse-derived DCPs were differentiated for two days in IL-15 DC medium as described in Example 1, and transduced with LV-optE6E7 or LV-optE6E7 plus LV-calnexin. BALB/c mice bearing CT26/optE6E7 tumors were divided into two groups of five mice each group, and received two DC vaccinations at a one-week interval. It was observed that mice injected with DCs modified by LV-optE6E7 plus LV-calnexin displayed increased survival rate than those modified by LV-optE6E7 alone (FIG. 6B), a result consistent with previous findings using BM-derived IL-4 DCs [35].

Example 3

Discussion Related to Examples 1 and 2

The access to good quality and sufficient amount of functional DCs is critical to the success of immunotherapy against cancer and infections. In such settings, it is desirable to generate a large number of DCs capable of activating antigen-specific effector T cells but not T regulatory cells (Tregs). For examples, infusion of myeloid DCs and systemic administration of IL-2 have been shown to induce and expand CD4+FoxP3+ Tregs in myeloma and renal cancer patients [31, 40-42]. Presented herein is a reliable and highly reproducible strategy based on expansion of CD34+ HPCs as well as differentiation of a unique lineage of functional DC progenitors (DCPs) using stromal cells engineered with lentivectors encoding multiple growth factors. The ex vivo generated DCs exhibited canonical antigen presentation functions including antigen uptake, processing and activation of T cells and in vivo anti-cancer effects.

The CD34+ HPCs constitute a heterogeneous cell population that can generate various lineages of DCs [10, 15, 19, 43, 44]. A culture condition was adopted which supports expansion of CD34+ HPCs and DC differentiation through the combination of cell-free and cell-associated signals including those supporting hematopoietic stem cell proliferation (KL, FL, TPO, IL-3, IL-6, bFGF), myeloid DC differentiation (GM-CSF), as well as IL-15 which is known to promote leukocyte survival and expansion. This unique ex vivo culture condition supports expansion of a novel lineage of DCs that are different from the conventional myeloid DCs. It is plausible that the continued renewal of differentiating DCPs in such a system was due to the lack of IL-4 and TNF-α, the two common growth factors used in many reported methods and known to induce DC maturation and block proliferation thus limiting their expansion [30]. This novel lineage of DCs is different from the commonly known IL-4 DCs or IL-15 DCs. Multiplex cytokine and chemokine array analysis suggests that DCPs resemble IL-15 DCs except that DCPs expressed less TNFα and IFN-γ, but much higher levels of inflammatory cytokines (IL-1a, IL-1b, and IL-6) associated with high levels of chemotactic factors (GRO-α and MCP-1) as compared with IL-15 DCs (Table 1). The beadchip microarray analysis of gene expression profile indicates that the ex vivo differentiated DCPs share a common DC progenitor but branched in between the peripheral blood adherent cell-derived IL-4 DCs and IL-15 DCs (FIG. 4). Functional analysis shows that DCP-DCs are fully capable of antigen presentation and stimulation of antigen-specific T cells. It is concluded that the ex vivo derived DCP-DCs represent a unique lineage of DCs displaying phenotype and function between IL-4 DCs that have prominent adaptive immune functions, and IL-15 DCs that have prominent innate immune functions.

Several studies have reported that in addition to KL, FL and TPO, other growth factors including bFGF, bone morphogenetic protein 4 (BMP4), IL-3, IL-6 or stromal cell derived factor-1 (SDF-1 or CXCL12) can help increase $CD34^+$ HPC expansion and maintain their undifferentiated state [45-47]. Epigenetic modification using DNA methyltransferase (DNMT) inhibitor 5-azacytidine (5-aza) and/or histone acetylase inhibitor trichostatin A (TSA) can block differentiation of hematopoietic stem cells and moderately promote their expansion [48]. Supplementation of these factors in the LSC system, however, does not further increase HPC expansion potential (data not shown). Nevertheless, this ex vivo system offers a convenient and reproducible two-dimensional culture system for the study of self-renewal and development of human HSC and DC. Analysis of additional regulatory factors can be easily integrated into this culture system.

The development and maturation of DCs in cancer patients may be functionally defective, resulting in reduced expression of class II MHC and diminished antigen cross-priming activity [7, 49-51]. In a previous report, it was shown that IL-4 DCs from multiple myeloma patients can be functionally improved through upregulation of the chaperone protein calnexin, which substantially increases the secretion of inflammatory cytokines and chemokines accompanied by a strong memory T cell response [31, 35]; DCP-DCs, as illustrated here, may accomplish the same without further modifications. As IL-15 has been shown to reduce Treg activities and increase antigen-specific CD8 T cell response in vitro and in vivo, the ex vivo generated DCP-DCs have potential of overcoming DC dysfunctions in cancer patients [26, 52, 53]. DCPs from cancer patients including multiple myeloma, acute myeloid leukemia, acute lymphoblastic leukemia, Hodgkin's lymphoma and glioblastoma patients have been successfully generated from a small number of BM $CD34^+$ HPCs over several orders of magnitude ($>10^6$) (unpublished). Thus, this ex vivo approach avoids potential immune suppressive microenvironment of DC development in patients. Further efforts in process development and standardization, and GMP validation of the feeder culture system are needed before DCP-DCs are ready for clinical trials.

This ex vivo DC development system supports a robust expansion of a novel DC lineage in culture from a small number of $CD34^+$ HPCs, which provides a critical solution to problems often encountered in immunotherapy.

LIST OF ABBREVIATIONS

BM, bone marrow; PB, peripheral blood; HPC, hematopoietic progenitor cell; PBM, peripheral blood monocyte; LSC, lentivector-modified stromal cell; LV, lentiviral vector; TPO, thrombopoietin; KL, kit-ligand; FL, Flt3-ligand; bFGF, basic fibroblast growth factor; DC, dendritic cell; DCP, DC progenitor; tNGFR, truncated nerve growth factor receptor; BLCL, B lymphoblastoid cell line; ICCS, intracellular cytokine staining.

REFERENCES

1. Farkas A, Conrad C, Tonel G, Borbenyi Z, Kemeny L, Dobozy A, Nestle F O: Current state and perspectives of dendritic cell vaccination in cancer immunotherapy. *Skin Pharmacol Physiol* 2006, 19:124-131.
2. Talarn C, Urbano-Ispizua A, Martino R, Batlle M, Fernandez-Aviles F, Herrera C, Perez-Simon J A, Gaya A, Aymerich M, Petriz J, et al: G-CSF increases the number of peripheral blood dendritic cells CD16+ and modifies the expression of the costimulatory molecule CD86+. *Bone Marrow Transplant* 2006, 37:873-879.
3. Menetrier-Caux C, Montmain G, Dieu M C, Bain C, Favrot M C, Caux C, Blay J Y: Inhibition of the differentiation of dendritic cells from CD34(+) progenitors by tumor cells: role of interleukin-6 and macrophage colony-stimulating factor. *Blood* 1998, 92:4778-4791.
4. Ninomiya T, Akbar S M, Masumoto T, Horiike N, Onji M: Dendritic cells with immature phenotype and defective function in the peripheral blood from patients with hepatocellular carcinoma. *J Hepatol* 1999, 31:323-331.
5. Brown R D, Pope B, Murray A, Esdale W, Sze D M, Gibson J, Ho P J, Hart D, Joshua D: Dendritic cells from patients with myeloma are numerically normal but functionally defective as they fail to up-regulate CD80 (B7-1) expression after huCD40LT stimulation because of inhibition by transforming growth factor-beta1 and interleukin-10. *Blood* 2001, 98:2992-2998.
6. Peguet-Navarro J, Sportouch M, Popa I, Berthier O, Schmitt D, Portoukalian J: Gangliosides from human melanoma tumors impair dendritic cell differentiation from monocytes and induce their apoptosis. *J Immunol* 2003, 170:3488-3494.
7. Gabrilovich D: Mechanisms and functional significance of tumour-induced dendritic-cell defects. *Nat Rev Immunol* 2004, 4:941-952.
8. Gervais A, Leveque J, Bouet-Toussaint F, Burtin F, Lesimple T, Sulpice L, Patard J J, Genetet N, Catros-Quemener V: Dendritic cells are defective in breast cancer patients: a potential role for polyamine in this immunodeficiency. *Breast Cancer Res* 2005, 7:R326-335.
9. Gottfried E, Kreutz M, Mackensen A: Tumor-induced modulation of dendritic cell function. *Cytokine Growth Factor Rev* 2008, 19:65-77.
10. Wu L, D'Amico A, Hochrein H, O'Keeffe M, Shortman K, Lucas K: Development of thymic and splenic dendritic cell populations from different hemopoietic precursors. *Blood* 2001, 98:3376-3382.
11. MacDonald K P, Munster D J, Clark G J, Dzionek A, Schmitz J, Hart D N: Characterization of human blood dendritic cell subsets. *Blood* 2002, 100:4512-4520.
12. Shortman K, Liu Y J: Mouse and human dendritic cell subtypes. *Nat Rev Immunol* 2002, 2:151-161.
13. Chicha L, Jarrossay D, Manz M G: Clonal type I interferon-producing and dendritic cell precursors are contained in both human lymphoid and myeloid progenitor populations. *J Exp Med* 2004, 200:1519-1524.
14. Blom B, Spits H: Development of human lymphoid cells. *Annu Rev Immunol* 2006, 24:287-320.
15. Geissmann F, Manz M G, Jung S, Sieweke M H, Merad M, Ley K: Development of monocytes, macrophages, and dendritic cells. *Science* 2010, 327:656-661.

16. Zenke M, Hieronymus T: Towards an understanding of the transcription factor network of dendritic cell development. *Trends Immunol* 2006, 27:140-145.
17. Canque B, Camus S, Dalloul A, Kahn E, Yagello M, Dezutter-Dambuyant C, Schmitt D, Schmitt C, Gluckman J C: Characterization of dendritic cell differentiation pathways from cord blood CD34(+)CD7(+)CD45RA(+) hematopoietic progenitor cells. *Blood* 2000, 96:3748-3756.
18. Hao Q L, Zhu J, Price M A, Payne K J, Barsky L W, Crooks G M: Identification of a novel, human multilymphoid progenitor in cord blood. *Blood* 2001, 97:3683-3690.
19. Ferlazzo G, Klein J, Paliard X, Wei W Z, Galy A: Dendritic cells generated from CD34+ progenitor cells with flt3 ligand, c-kit ligand, GM-CSF, IL-4, and TNF-alpha are functional antigen-presenting cells resembling mature monocyte-derived dendritic cells. *J Immunother* 2000, 23:48-58.
20. Chen X, He J, Chang L-J: Alteration of T cell immunity by lentiviral transduction of human monocyte-derived dendritic cells. *Retrovirology* 2004, 1:37.
21. Curti A, Fogli M, Ratta M, Tura S, Lemoli R M: Stem cell factor and FLT3-ligand are strictly required to sustain the long-term expansion of primitive CD34+DR- dendritic cell precursors. *J Immunol* 2001, 166:848-854.
22. Caux C, Vanbervliet B, Massacrier C, Dezutter-Dambuyant C, de Saint-V is B, Jacquet C, Yoneda K, Imamura S, Schmitt D, Banchereau J: CD34+ hematopoietic progenitors from human cord blood differentiate along two independent dendritic cell pathways in response to GM-CSF+TNF alpha. *J Exp Med* 1996, 184:695-706.
23. Mohamadzadeh M, Berard F, Essert G, Chalouni C, Pulendran B, Davoust J, Bridges G, Palucka A K, Banchereau J: Interleukin 15 skews monocyte differentiation into dendritic cells with features of Langerhans cells. *J Exp Med* 2001, 194:1013-1020.
24. Pulendran B, Dillon S, Joseph C, Curiel T, Banchereau J, Mohamadzadeh M: Dendritic cells generated in the presence of GM-CSF plus IL-15 prime potent CD8+ Tcl responses in vivo. *Eur J Immunol* 2004, 34:66-73.
25. Schluns K S, Lefrancois L: Cytokine control of memory T-cell development and survival. *Nat Rev Immunol* 2003, 3:269-279.
26. Dubois S P, Waldmann T A, Muller J R: Survival adjustment of mature dendritic cells by IL-15. *Proc Natl Acad Sci USA* 2005, 102:8662-8667.
27. Anguille S, Smits E L, Cools N, Goossens H, Berneman Z N, Van Tendeloo V F: Short-term cultured, interleukin-15 differentiated dendritic cells have potent immunostimulatory properties. *J Transl Med* 2009, 7:109.
28. Hardy M Y, Kassianos A J, Vulink A, Wilkinson R, Jongbloed S L, Hart D N, Radford K J: NK cells enhance the induction of CTL responses by IL-15 monocyte-derived dendritic cells. *Immunol Cell Biol* 2009, 87:606-614.
29. Liu A, Takahashi M, Narita M, Zheng Z, Kanazawa N, Abe T, Nikkuni K, Furukawa T, Toba K, Fuse I, Aizawa Y: Generation of functional and mature dendritic cells from cord blood and bone marrow CD34+ cells by two-step culture combined with calcium ionophore treatment. *J Immunol Methods* 2002, 261:49-63.
30. Slukvin I I, Vodyanik M A, Thomson J A, Gumenyuk M E, Choi K D: Directed differentiation of human embryonic stem cells into functional dendritic cells through the myeloid pathway. *J Immunol* 2006, 176:2924-2932.
31. Han S, Wang B, Cotter M J, Yang L J, Zucali J, Moreb J S, Chang L-J: Overcoming immune tolerance against multiple myeloma with lentiviral calnexin-engineered dendritic cells. *Mol Ther* 2008, 16:269-279.
32. Chang L-J, Urlacher V, Iwakuma T, Cui Y, Zucali J: Efficacy and safety analyses of a recombinant human immunodeficiency virus type 1 derived vector system. *Gene Therapy* 1999, 6:715-728.
33. Chang L-J, Zaiss A-K: Self inactivating lentiviral vectors in combination with a sensitive Cre/loxP reporter system. In *Methods in Molecular Medicine*. Edited by Walker J: Humana Press Inc.; 2001: 367-382: *Viral Vectors for Gene Therapy: Methods and Protocols*].
34. Zaiss A-K, Son S, Chang L-J: RNA 3'-readthrough of oncoretrovirus and lentivirus: implications in vector safety and efficacy. *Journal of Virology* 2002, 76:7209-7219.
35. Wang B, Han S, Lien L, Chang L-J: Lentiviral calnexin-modified dendritic cells promote expansion of high-avidity effector T cells with central memory phenotype *Immunology* 2009, 128:43-57.
36. Han S, Chang L P Immunity of lentiviral vector-modified dendritic cells. *Methods Mol Biol* 2009, 542:245-259.
37. Han S, Huang Y, Liang Y, Ho Y, Wang Y, Chang L-J: Phenotype and functional evaluation of ex vivo generated antigen-specific immune effector cells with potential for therapeutic applications. *Journal of Hematology and Oncology* 2009, 2:34.
38. Wang B, He J, Liu C, Chang L J: An effective cancer vaccine modality: Lentiviral modification of dendritic cells expressing multiple cancer-specific antigens. *Vaccine* 2006, 24:3477-3489.
39. Gammaitoni L, Bruno S, Sanavio F, Gunetti M, Kollet O, Cavalloni G, Falda M, Fagioli F, Lapidot T, Aglietta M, Piacibello W: Ex vivo expansion of human adult stem cells capable of primary and secondary hemopoietic reconstitution. *Exp Hematol* 2003, 31:261-270.
40. Yamazaki S, Iyoda T, Tarbell K, Olson K, Velinzon K, Inaba K, Steinman R M: Direct expansion of functional CD25+ CD4+ regulatory T cells by antigen-processing dendritic cells. *J Exp Med* 2003, 198:235-247.
41. Banerjee D K, Dhodapkar M V, Matayeva E, Steinman R M, Dhodapkar K M: Expansion of FOXP3high regulatory T cells by human dendritic cells (DCs) in vitro and after injection of cytokine-matured DCs in myeloma patients. *Blood* 2006, 108:2655-2661.
42. Lemoine F M, Cherai M, Giverne C, Dimitri D, Rosenzwajg M, Trebeden-Negre H, Chaput N, Barrou B, Thioun N, Gattegnio B, et al: Massive expansion of regulatory T-cells following interleukin 2 treatment during a phase I-II dendritic cell-based immunotherapy of metastatic renal cancer. *Int J Oncol* 2009, 35:569-581.
43. Luft T, Pang K C, Thomas E, Bradley C J, Savoia H, Trapani J, Cebon J: A serum-free culture model for studying the differentiation of human dendritic cells from adult CD34+ progenitor cells. *Exp Hematol* 1998, 26:489-500.
44. Strobl H: Molecular mechanisms of dendritic cell sub-lineage development from human hematopoietic progenitor/stem cells. *Int Arch Allergy Immunol* 2003, 131:73-79.
45. Bryder D, Jacobsen S E: Interleukin-3 supports expansion of long-term multilineage repopulating activity after multiple stem cell divisions in vitro. *Blood* 2000, 96:1748-1755.
46. Hutton J F, Rozenkov V, Khor F S, D'Andrea R J, Lewis I D: Bone morphogenetic protein 4 contributes to the maintenance of primitive cord blood hematopoietic progenitors in an ex vivo stroma-noncontact co-culture system. *Stem Cells Dev* 2006, 15:805-813.
47. Hwang J H, Kim S W, Park S E, Yun H J, Lee Y, Kim S, Jo D Y: Overexpression of stromal cell-derived factor-1 enhances endothelium-supported transmigration, maintenance, and proliferation of hematopoietic progenitor cells. *Stem Cells Dev* 2006, 15:260-268.
48. Milhem M, Mahmud N, Lavelle D, Araki H, Desimone J, Saunthararajah Y, Hoffman R: Modification of Hematopoietic Stem Cell Fate By 5aza 2' deoxycytidine and Trichostatin A. *Blood* 2004.
49. Almand B, Clark J I, Nikitina E, van Beynen J, English N R, Knight S C, Carbone D P, Gabrilovich D I: Increased Production of Immature Myeloid Cells in Cancer Patients: A Mechanism of Immunosuppression in Cancer. *J Immunol* 2001, 166:678-689.
50. Menetrier-Caux C, Thomachot M C, Alberti L, Montmain G, Blay J Y: IL-4 Prevents the Blockade of Dendritic Cell Differentiation Induced by Tumor Cells. *Cancer Res* 2001, 61:3096-3104.
51. Gerner M Y, Casey K A, Mescher M F: Defective MHC class II presentation by dendritic cells limits CD4 T cell help for antitumor CD8 T cell responses. *J Immunol* 2008, 181:155-164.
52. Rubinstein M P, Kadima A N, Salem M L, Nguyen C L, Gillanders W E, Cole D J: Systemic administration of IL-15 augments the antigen-specific primary CD8+ T cell response following vaccination with peptide-pulsed dendritic cells. *J Immunol* 2002, 169:4928-4935.
53. Klebanoff C A, Finkelstein S E, Surman D R, Lichtman M K, Gattinoni L, Theoret M R, Grewal N, Spiess P J, Antony P A, Palmer D C, et al: IL-15 enhances the in vivo antitumor activity of tumor-reactive CD8+ T cells. *Proc Natl Acad Sci USA* 2004, 101:1969-1974.

It should be borne in mind that all patents, patent applications, patent publications, technical publications, scientific publications, and other references referenced herein and in the accompanying appendices are hereby incorporated by reference in this application to the extent not inconsistent with the teachings herein.

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the following definitions are provided.

While a number of embodiments of the present invention have been shown and described herein in the present context, such embodiments are provided by way of example only, and not of limitation. Numerous variations, changes and substitutions will occur to those skilled in the art without materially departing from the invention herein. For example, the present invention need not be limited to best mode disclosed herein, since other applications can equally benefit from the teachings of the present invention. Also, in the claims, means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

APPENDIX

Additional File 1—

Supplemental Table 1. Antibodies and their specific clones: All antibodies were purchased from BD PharMingen, Invitrogen CALTAG laboratories, eBiosciences and Cell Signaling.

Additional File 2—

Supplemental Table 2. Primer sequences for cDNA cloning and RT-PCR.

TABLE 1

Analysis of cytokines and chemokines secreted by mature DCs

| Cytokines/Chemokines | IL-4 DCs (pg/ml) | IL-15 DCs (pg/ml) | DCPs (pg/ml) |
| --- | --- | --- | --- |
| IL-1α | 135 (32) | 332 (1,228) ↑ | 1,202 (239) ↑ |
| IL-1β | 338 (92) | 601 (2,696) ↑ | 8,582 (2,440) ↑↑ |
| IL-2 | 6 (5) | 7 (7) | 6 (4) |
| IL-4 | 3 (3) | 2 (4) | 2 (1) ↓ |
| IL-5 | 2 (1) | 4 (7) ↑ | 9 (6) ↑ |
| IL-6 | 652 (53) | 1,664 (8,036) ↑ | 43,607 (4,605) ↑↑ |
| IL-8 | 154,440 (55,237) | 155,499 (297,615) ↑ | 303,222 (286,234) ↑ |
| IL-10 | 68 (53) | 7 (114) | 110 (162) ↑ |
| IL-12p70 | 6 (3) | 16 (25) ↑ | 8 (6) ↑ |
| IL-13 | 6 (5) | 170 (148) ↑↑ | 10 (11) ↑ |
| IL-15 | 25 (23) | 2,359 (248) ↑↑ | 87 (81) ↑ |
| IL-17 | 8 (4) | 12 (13) ↑ | 5 (6) |
| IL-23 | 17 (30) | 79 (90) ↑ | 215 (36) ↑ |
| IFN-γ | <1 (<1) | 2,331 (1,905) ↑↑ | <1 (1) |
| TNFα | 149 (72) | 1,439 (3,152) ↑↑ | 226 (70) |
| TNFβ | <1 (2) | 87 (67) ↑ | 3 (6) ↑ |
| Eotaxin | 2 (3) | 3 (3) | 4 (2) |
| GRO-α | 8,394 (2,158) | 2,142 (15,744) | 131,310 (19,241) ↑↑ |
| I-309 | 1,989 (533) | 15,086 (28,758) ↑ | 18,141 (42,805) ↑↑ |
| MCP-1 | 342 (571) | 547 (4,971) ↑ | 184,457 (127,001) ↑↑ |
| MCP-2 | 11 (9) | 339 (2,512) ↑↑ | 2,381 (46) ↑ |

TABLE 1-continued

Analysis of cytokines and chemokines secreted by mature DCs

| Cytokines/Chemokines | IL-4 DCs (pg/ml) | IL-15 DCs (pg/ml) | DCPs (pg/ml) |
|---|---|---|---|
| RANTES | 1,588 (179) | 2,552 (1,875) ↑ | 1,666 (3,085) ↑ |
| TARC | 469,352 (337,109) | 1,783 (1,636) ⇓ | 20,739 (14,855) ⇓ |

Results are averages of triplicate analyses of cytokines and chemokines (pg/ml/$10^6$ cells/24 hr) secreted by mature DCs of two donors (the 2$^{nd}$ donor shown in parenthesis) using multiplex ELISA arrays. Up- (↑) and down-regulations (↓) are depicted by arrows, and double arrows indicate a difference more than ten-fold from the IL-4 DCs.

TABLE 2

Primer sequences for cDNA cloning and RT-PCR.

| Primer name | Primer sequence (5' to 3') |
|---|---|
| hIL-3 RT-PCR F | TGATCGACGAGATCATCACC |
| hIL-3 RT-PCR R | GCAGGTTCTTCAGGATGCTC |
| hIL-6 ORF F | AAGGATCCACCATGAACTCCTTCTCCACAAGC |
| hIL-6 ORF R | AAACTAGTCTACATTTGCCGAAGAGCC |
| hIL-6 RT-PCR F | GTAGCCGCCCCACACAGACAGCC |
| hIL-6 RT-PCR R | GCCATCTTTGGAAGGTTCAGG |
| hIL-15 ORF F | TTGGATCCACCATGAGAATTTCGAAACCACATTTG |
| hIL-15 ORF R | TTACTAGTCAAGAAGTGTTGATGAAC |
| hIL-15 RT-PCR F | AGCTGGCATTCATGTCTTCA |
| hIL-15 RT-PCR R | ACTTTGCAACTGGGGTGAAC |
| hGM-CSF ORF F | CCCGGGAAGCTTCCACCATGTGGCTGCAGAGCCTG |
| hGM-CSF ORF R | AATGGATCCTATCACTCCTGGACTGGCTC |
| hGM-CSF RT-PCR F | ATGTGAATGCCATCCAGGAG |
| hGM-CSF RT-PCR R | AGGGCAGTGCTGCTTGTAGT |
| mGM-CSF ORF F | AAT CTA GAC CAC CAT GTG GCT GCA GAA TTT AC |
| mGM-CSF ORF R | AAGAATTCCTCATTTTTGGACTGG |
| mGM-CSF RT-PCR F | GGCCTTGGAAGCATGTAGAG |
| mGM-CSF RT-PCR R | CCGTAGACCCTGCTCGAATA |
| hbFGF ORF F | AAGGATCCACCATGGTGGGTGTCGGGGTGGAG |
| hbFGF ORF R | AAACTAGTCAGCTCTTAGCAGACATTG |
| hbFGF RT-PCR F | ATGGCAGCCGGGAGCATCACCACGC |
| hbFGF RT-PCR R | CAGCTCTTAGCAGACATTGGAAGAAAAG |
| hSCF ORF F | TTTCTAGACCACCATGAAGAAGACACAAACTTG |
| hSCF ORF R | CCGGATCCTTACACTTCTTGAAACTC |
| hSCF RT-PCR F | CTCCTATTTAATCCTCTCGTC |
| hSCF RT-PCR R | TACTACCATCTCGCTTATCCA |
| hFlt3-L ORF F | AAGGATCCGCAGGATGAGGCCTTGG |
| hFlt3-L ORF R | CCCAGGATGAGGCCTTGG |
| hFlt3-L RT-PCR F | GCT TCA AGA TTA CCC AGT CAC C |
| hFlt3-L RT-PCR R | GAC CCA GCG ACA GTC TTG A |
| hTPO ORF F | TTTCTAGACCACCATGGAGCTGACTGAATTG |
| hTPO ORF R | TTGAATTCTTACCCTTCCTGAGACAG |
| hTPO RT-PCR F | GAA TGG AAA ACC CAG ATG GA |
| hTPO RT-PCR R | AGG GAT GAG AGG CAA GTG G |
| EBV BMLF ORF F | AAGGATCCACCATGGAGGGCAGCGAAGAACAC |
| EBV BMLF ORF R | AAA CTA GTT ATT GAT TTA ATC CAG GAA C |
| hCCL17 RT-PCR F | ATG GCC CCA CTG AAG ATG CTT |
| hCCL17 RT-PCR R | TGA ACA CCA ACG GTG GAG G |
| hPU.1 RT-PCR F | TGG AAG GGT TTC CCC TCG TC |
| hPU.1 RT-PCR R | TGC TGT CCT TCA TGT CGC CG |
| hCCR6 RT-PCR F | GGGGGAATATTCTGGTGGTGA |
| hCCR6 RT-PCR R | CATCGCTGCCTTGGGTGTTGTAT |
| hE-CAD RT-PCR F | TCTACAGCATCACTGCCCAAGGAGCTG |
| hE-CAD RT-PCR R | AGCTTGAACCACCAGGGTATACGTAGG |
| hLangerine RT-PCR F | GCTTGGAGAATATGAGCAAGTTGC |
| hLangerine RT-PCR R | GCACTTTGGACCTTGTTGAATGGC |
| hId2 RT-PCR F | ACGACCCGATGAGCCTGCTA |
| hId2 RT-PCR R | TCCTGGAGCGCTGGTTCTG |
| hIL7Ra RT-PCR F | ATTCAAGCTAGAGATGAAGTG |
| hIL7Ra RT-PCR F | TTACTCTTTCATTCTTTCCTC |
| PreT RT-PCR F | AGT ACA CAG CCC ATG CAT CTG TCA |
| PreT RT-PCR R | AAT GCT CCA AGA CTG GAG GAA GGA |
| mGAPDH RT-PCR F | TCACCACCATGGAGAAGGC |
| mGAPDH RT-PCR R | GCTAAGCAGTTGGTGGTGCA |

ORF, open reading frame; F, forward; R, reverse.

What is claimed is:

1. A method of producing dendritic cell (DC) progenitor cells, said method comprising:
   culturing a population of hematopoietic stem/progenitor cells (HPCs) in a first feeder culture comprising kit ligand (KL), fms-like tyrosine kinase 3 ligand (FL), thrombopoietin (TPO), IL-3, IL-6 and basic fibroblast growth factor (bFGF) under conditions to produce a population of first expanded cells; wherein the first feeder culture does not comprise GM-CSF or IL-15;
   culturing said first expanded cells in a second feeder culture comprising KL, FL, TPO, IL-3, IL-6, bFGF, GM-CSF and IL-15 under conditions to produce DC progenitor cells (DCPs).

2. The method of claim 1, wherein the first feeder culture comprises cells engineered to produce KL, FL, TPO, IL-3, IL-6 and/or bFGF.

3. The method of claim 2, wherein said first feeder culture comprises cells engineered via a viral vector comprising an expression construct comprising a sequence encoding KL, FL, TPO, IL-3, IL-6 and/or bFGF.

4. The method of claim 1, wherein the second feeder culture comprises cells engineered to produce KL, FL, TPO, GM-CSF, and/or IL-15.

5. The method of claim 1, wherein said first expanded cells possess HPC phenotypic characteristics.

6. The method of claim 1, further comprising culturing said DC progenitor cells in a third culture supplemented with GM-CSF and IL-15 under conditions to produce a population of cells having a phenotype similar to myeloid DCs.

7. The method of claim 6, wherein the third culture is feeder free.

* * * * *

SEQUENCE LISTING

<160> NUMBER OF SEQ ID NOS: 54

<210> SEQ ID NO 1
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 1
tgatcgacga gatcatcacc        20

<210> SEQ ID NO 2
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 2
gcaggttctt caggatgctc        20

<210> SEQ ID NO 3
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 3
aaggatccac catgaactcc ttctccacaa gc        32

<210> SEQ ID NO 4
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 4
aaactagtct acatttgccg aagagcc        27

<210> SEQ ID NO 5
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 5
gtagccgccc cacacagaca gcc        23

<210> SEQ ID NO 6
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 6
gccatctttg gaaggttcag g        21

<210> SEQ ID NO 7
<211> LENGTH: 35
<212> TYPE: DNA
<213> ORGANISM: Artificial Sequence

```
<220> FEATURE:
<223> OTHER INFORMATION: Synthetic Polynucleotide

<400> SEQUENCE: 7
ttggatccac catgagaatt tcgaaaccac atttg                              35

<210> SEQ ID NO 8
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 8
ttactagtca agaagtgttg atgaac                                        26

<210> SEQ ID NO 9
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 9
agctggcatt catgtcttca                                               20

<210> SEQ ID NO 10
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 10
actttgcaac tggggtgaac                                               20

<210> SEQ ID NO 11
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 11
cccgggaagc ttccaccatg tggctgcaga gcctg                              35

<210> SEQ ID NO 12
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 12
aatggatcct atcactcctg gactggctc                                     29

<210> SEQ ID NO 13
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 13
atgtgaatgc catccaggag                                               20
```

<210> SEQ ID NO 14
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 14
agggcagtgc tgcttgtagt                                            20

<210> SEQ ID NO 15
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 15
aatctagacc accatgtggc tgcagaattt ac                              32

<210> SEQ ID NO 16
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 16
aagaattcct cattttgga ctgg                                        24

<210> SEQ ID NO 17
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 17
ggccttggaa gcatgtagag                                            20

<210> SEQ ID NO 18
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 18
ccgtagaccc tgctcgaata                                            20

<210> SEQ ID NO 19
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 19
aaggatccac catggtgggt gtcggggtg gag                              33

<210> SEQ ID NO 20
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 20
aaactagtca gctcttagca gacattg                                   27

<210> SEQ ID NO 21
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 21
atggcagccg ggagcatcac cacgc                                     25

<210> SEQ ID NO 22
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 22
cagctcttag cagacattgg aagaaaaag                                 29

<210> SEQ ID NO 23
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 23
tttctagacc accatgaaga agacacaaac ttg                            33

<210> SEQ ID NO 24
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 24
ccggatcctt acacttcttg aaactc                                    26

<210> SEQ ID NO 25
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 25
ctcctattta atcctctcgt c                                         21

<210> SEQ ID NO 26
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 26
tactaccatc tcgcttatcc a                                         21

<210> SEQ ID NO 27

```
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 27
aaggatccgc aggatgaggc cttg                                              24

<210> SEQ ID NO 28
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 28
cccaggatga ggccttgg                                                     18

<210> SEQ ID NO 29
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 29
gcttcaagat tacccagtca cc                                                22

<210> SEQ ID NO 30
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 30
gacccagcga cagtcttga                                                    19

<210> SEQ ID NO 31
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 31
tttctagacc accatggagc tgactgaatt g                                      31

<210> SEQ ID NO 32
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 32
ttgaattctt acccttcctg agacag                                            26

<210> SEQ ID NO 33
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 33
```
gaatggaaaa cccagatgga                                              20

<210> SEQ ID NO 34
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 34
agggatgaga ggcaagtgg                                               19

<210> SEQ ID NO 35
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 35
aaggatccac catggagggc agcgaagaac ac                                32

<210> SEQ ID NO 36
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 36
aaactagtta ttgatttaat ccaggaac                                     28

<210> SEQ ID NO 37
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 37
atggccccac tgaagatgct t                                            21

<210> SEQ ID NO 38
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 38
tgaacaccaa cggtggagg                                               19

<210> SEQ ID NO 39
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 39
tggaagggtt tcccctcgtc                                              20

<210> SEQ ID NO 40
<211> LENGTH: 20
<212> TYPE: DNA

```
<213> ORGANISM: Artificial Sequence
<220> FEATURE:
<223> OTHER INFORMATION: Synthetic Polynucleotide

<400> SEQUENCE: 40
tgctgtcctt catgtcgccg                                              20

<210> SEQ ID NO 41
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 41
gggggaatat tctggtggtg a                                            21

<210> SEQ ID NO 42
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 42
catcgctgcc ttgggtgttg tat                                          23

<210> SEQ ID NO 43
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 43
tctacagcat cactgcccaa ggagctg                                      27

<210> SEQ ID NO 44
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 44
agcttgaacc accagggtat acgtagg                                      27

<210> SEQ ID NO 45
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 45
gcttggagaa tatgagcaag ttgc                                         24

<210> SEQ ID NO 46
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 46
gcactttgga ccttgttgaa tggc                                         24
```

<210> SEQ ID NO 47
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 47
acgacccgat gagcctgcta                                           20

<210> SEQ ID NO 48
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 48
tcctggagcg ctggttctg                                            19

<210> SEQ ID NO 49
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 49
attcaagcta gagatgaagt g                                         21

<210> SEQ ID NO 50
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 50
ttactctttc attctttcct c                                         21

<210> SEQ ID NO 51
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 51
agtacacagc ccatgcatct gtca                                      24

<210> SEQ ID NO 52
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 52
aatgctccaa gactggagga agga                                      24

<210> SEQ ID NO 53
<211> LENGTH: 19
<212> TYPE: DNA
<213> ORGANISM: Artificial Sequence
<220> FEATURE:

```
<223> OTHER INFORMATION: Synthetic Polynucleotide

<400> SEQUENCE: 53
tcaccaccat ggagaaggc                                                      19

<210> SEQ ID NO 54
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 54
gctaagcagt tggtggtgca                                                     20
```